(12) United States Patent
Takahashi (10) Patent No.: US 8,220,993 B2
(45) Date of Patent: Jul. 17, 2012

(54) RADIOGRAPHIC APPARATUS

(75) Inventor: Kenji Takahashi, Kanagawa-ken (JP)

(73) Assignee: Fujifilm Corporation (JP)

( * ) Notice: Subject to any disclaimer, the term of this patent is extended or adjusted under 35 U.S.C. 154(b) by 356 days.

(21) Appl. No.: 12/697,965

(22) Filed: Feb. 1, 2010

(65) Prior Publication Data
US 2010/0195796 A1 Aug. 5, 2010

(30) Foreign Application Priority Data
Feb. 3, 2009 (JP) ................................. 2009-022115

(51) Int. Cl.
*G01D 18/00* (2006.01)
(52) U.S. Cl. ................................ 378/207; 378/9; 378/92
(58) Field of Classification Search ................ 378/9, 19, 378/91, 92, 98, 98.8, 207
See application file for complete search history.

(56) References Cited

U.S. PATENT DOCUMENTS
| | | | |
|---|---|---|---|
| 7,978,816 B2 * | 7/2011 | Matsuura et al. | ............... 378/62 |
| 2007/0133747 A1 | 6/2007 | Manak et al. | |
| 2009/0316860 A1 | 12/2009 | Okunuki et al. | |

* cited by examiner

*Primary Examiner* — Jurie Yun
(74) *Attorney, Agent, or Firm* — Studebaker & Brackett PC; Donald R. Studebaker (57) ABSTRACT

Fan beams of radiation are output from a multiplicity of radiation sources. Radiation is output simultaneously only from a part of the radiation sources having irradiation ranges that neither overlap with each other nor are adjacent to each other. Image correction data corresponding to each group of radiation sources is obtained by sequentially outputting radiation to the radiographic image detector while the groups of radiation sources are sequentially switched without setting a subject. An effective area that has a value higher than a predetermined threshold value is determined for each image correction data. Radiation is sequentially output to the radiographic image detector in a state in which a subject is set while groups of radiation sources are switched. Radiation image data obtained based on the effective area, and which corresponds to each of the groups of radiation sources, is corrected based on the image correction data.

5 Claims, 7 Drawing Sheets

RADIOGRAPHIC APPARATUS

BACKGROUND OF THE INVENTION

1. Field of the Invention

The present invention relates to a radiographic apparatus in which a multiplicity of radiation sources that output radiation are dispersedly arranged.

2. Description of the Related Art

Conventionally, a radiographic apparatus using a multi-X-ray generation apparatus was proposed. The multi-X-ray generation apparatus includes a multi-electron-output device in which a multiplicity of electron output devices are arranged, and outputs multi-X-ray beams by outputting electron beams from each of the electron output devices to a target (please refer to U.S. Patent Application Publication No. 20090316860 (Patent Literature 1), for example).

However, as in the radiographic apparatus disclosed in Patent Literature 1, when electron beams are simultaneously output from a multiplicity of electron output devices to simultaneously irradiate a subject with a plurality of X-ray beams, the irradiation ranges of the plurality of X-ray beams on an X-ray detector overlap with each other. Therefore, scattered rays that cause noises are generated, and the image qualities of radiographic images deteriorate. If the electron output devices are driven one by one to output the electron beams, the influence of the scattered rays may be prevented. However, the length of time for outputting electron beams from all of the electron output devices becomes long, and a long time period is required to perform radiography.

The specification of U.S. Patent Application Publication No. 20070133747 (Patent Literature 2) also proposes a radiographic apparatus using a multi-X-ray generation apparatus that outputs multi-X-ray beams in a manner similar to the radiographic apparatus disclosed in Patent Literature 1. Patent Literature 2 proposes preventing an influence of scattered rays by dividing the irradiation range on the X-ray detector into two parts of houndstooth patterns so that the irradiation ranges of X-ray beams that are simultaneously output are not adjacent to each other on the X-ray detector.

However, even if the irradiation range of each of the X-ray beams is controlled as in the radiographic apparatus disclosed in Patent Literature 2, scattered rays overlap with each other in diagonal directions. Therefore, it is impossible to sufficiently prevent the influence of the scattered rays.

Further, in the radiographic apparatus disclosed in Patent Literature 2, a plurality of X-ray beams are output simultaneously, and the intensity of each of the plurality of X-ray beams is not always exactly the same. Since the intensities of the X-ray beams are not uniform, an uneven radiographic image may be obtained. Further, the irradiation ranges of X-rays are not always distributed as designed. When the irradiation ranges of X-rays are shifted, the image qualities of radiographic images may deteriorate.

SUMMARY OF THE INVENTION

In view of the foregoing circumstances, in a radiographic apparatus including a radiation output unit that outputs a plurality of radiation beams as described above, it is an object of the present invention to provide a radiographic apparatus that can sufficiently prevent an influence of scattered rays and that can suppress an influence of uneven intensities and uneven distribution of a plurality of radiation beams.

A radiographic apparatus of the present invention is a radiographic apparatus comprising:

a radiation output unit including a multiplicity of dispersedly-arranged radiation sources each outputting a fan beam of radiation that has a wide divergence direction and a narrow divergence direction in such a manner that cross sections of the fan beams of radiation showing the wide divergence directions are parallel to each other;

a radiographic image detector that detects the fan beam of radiation output from each of the multiplicity of dispersedly-arranged radiation sources of the radiation output unit;

a radiation output control unit that controls the radiation output unit in such a manner that the fan beams of radiation are output simultaneously only from each group of radiation sources, which are a part of the multiplicity of dispersedly-arranged radiation sources having irradiation ranges of the fan beams of radiation that neither overlap with each other nor are adjacent to each other on the radiographic image detector, and in such a manner that the groups of radiation sources are sequentially switched to output the radiation;

an image data obtainment unit that obtains image correction data corresponding to each of the groups of radiation sources, the image correction data being sequentially detected by the radiographic image detector by sequentially outputting the fan beams of radiation to the radiographic image detector while the radiation output control unit sequentially switches the groups of radiation sources without setting a subject between the radiation output unit and the radiographic image detector;

an effective area determination unit that determines, for each image correction data obtained by the image data obtainment unit, an effective area that has a value higher than a predetermined threshold value; and an image correction unit that corrects, based on the image correction data corresponding to each of the groups of radiation sources, radiographic image data corresponding to each of the groups of radiation sources that has been sequentially detected by the radiographic image detector by sequentially outputting the fan beams of radiation to the radiographic image detector while the radiation output control unit sequentially switches the groups of radiation sources in a state in which a subject is set between the radiation output unit and the radiographic image detector and that has been obtained based on the effective area.

Further, in the radiographic apparatus of the present invention, the radiographic image detector may include charge generation portions that generate charges corresponding to irradiation with the radiation, a multiplicity of two-dimensionally-arranged charge storage portions that store the charges generated in the charge generation portions, a multiplicity of signal lines each provided for each row of the multiplicity of two-dimensionally-arranged charge storage portions, and through which charge signals representing the charges stored in the multiplicity of two-dimensionally-arranged charge storage portions flow out, a multiplicity of switch devices that switch connections/disconnections between the multiplicity of signal lines and the multiplicity of two-dimensionally-arranged charge storage portions that correspond to the multiplicity of signal lines, the multiplicity of switch devices being provided for the charge storage portions respectively, and a multiplicity of scan lines each provided for each column of the multiplicity of two-dimensionally-arranged charge storage portions in such a manner that the multiplicity of scan lines are perpendicular to the multiplicity of signal lines, and through which control signals for turning on/off the multiplicity of switch devices are output. Further, the radiographic image detector and the radiation output unit may be arranged in such a manner that the wide divergence directions of the fan beams of radiation and the directions in which the multiplicity of scan lines extend are the same.

Here, the "charge storage portion" may utilize the capacity (capacitance) of a charge generation layer per se. Alternatively, a separately provided capacity may be utilized.

Further, the radiographic apparatus may include a scan signal control unit. The scan signal control unit reads out charge signals from charge storage portions on the radiographic image detector within a range corresponding to the effective area by sequentially outputting control signals for turning on switch devices to each of scan lines connected to columns of the charge storage portions within the range corresponding to the effective area. After reading out the charge signals, the scan signal control unit resets charge storage portions on the radiographic image detector outside the range corresponding to the effective area (in other words, charge storage portions that do not correspond to the effective area) by simultaneously outputting control signals for sequentially turning on switch devices to a plurality of scan lines that are connected to columns of the charge storage portions outside the range corresponding to the effective area.

Further, the radiographic apparatus may include a radiation source control unit that controls, based on the image correction data, each of the multiplicity of radiation sources in such a manner that the intensity of radiation output from each of the radiation sources belonging to the same group of radiation sources is similar to each other.

Further, the radiation sources may be arranged in such a manner that each total pixel value of pixels obtained by adding pixel signals at the same pixel positions of a plurality of pieces of image correction data obtained by the image data obtainment unit is substantially similar to each other. Further, the divergence angle of the fan beam output from each of the radiation sources may be set, and the intensity of the fan beam that is output from each of the radiation sources may be controlled.

According to the radiographic apparatus of the present invention, each of a multiplicity of radiation sources outputs a fan beam of radiation that has a wide divergence direction and a narrow divergence direction in such a manner that cross sections of the fan beams of radiation showing the wide divergence directions are parallel to each other. Further, the fan beams of radiation are output simultaneously only from each group of radiation sources, which are a part of the multiplicity of radiation sources having irradiation ranges of the fan beams of radiation that neither overlap with each other nor are adjacent to each other on the radiographic image detector. Therefore, it is possible to prevent an influence of scattered rays caused by a multiplicity of radiation beams that overlap with each other or are adjacent to each other. Further, since the fan beams that disperse widely only in one direction are used as described above, it is possible to efficiently prevent an influence of scattered rays.

Further, image correction data corresponding to each of the groups of radiation sources is obtained by the radiographic image detector by sequentially outputting fan beams of radiation to the radiographic image detector while the groups of radiation sources are sequentially switched without setting a subject. Further, an effective area that has a value higher than a predetermined threshold value is determined for each image correction data. Further, radiographic image data corresponding to each of the groups of radiation sources is sequentially detected by the radiographic image detector by sequentially outputting fan beams of radiation to the radiographic image detector while the groups of radiation sources are sequentially switched in a state in which a subject is set. Further, the radiographic image data that has been obtained based on the effective area is corrected based on the image correction data corresponding to each of the groups of radiation sources. Therefore, it is possible to exclude (remove) radiographic image data detected by irradiation with scattered rays. Further, it is possible to suppress an influence of uneven intensities and uneven distribution of a plurality of radiation beams.

Further, in the radiographic apparatus of the present invention, when the radiographic image detector and the radiation output unit are arranged in such a manner that the wide divergence directions of the fan beams of radiation output from each of the radiation sources and the directions in which the multiplicity of scan lines of the radiographic image detector extend are the same, the effective area and an area that is not the effective area can be specified by the scan line.

Further, for example, when charge signals are read out from charge storage portions on the radiographic image detector within a range corresponding to the effective area by sequentially outputting control signals for turning on switch devices to each of scan lines connected to columns of the charge storage portions within the range corresponding to the effective area, and after the charge signals are read out, charge storage portions on the radiographic image detector outside the range corresponding to the effective area are reset by simultaneously outputting control signals for sequentially turning on switch devices to a plurality of scan lines that are connected to columns of the charge storage portions outside the range corresponding to the effective area, it is possible to reduce the total time period for reading out the charge signals, compared with a case of reading out charge signals by sequentially switching all of the scan lines each time when fan beams of radiation are output from each of the groups of radiation sources. When the number of scan lines that are reset simultaneously is larger, a higher time reduction effect can be achieved. All of the scan lines may be reset simultaneously if current for resetting the scan lines does not cause any problems.

For example, when a group of radiation sources includes radiation sources arranged at intervals of n radiation sources (in other words, arranged at every (n+1)-th position), and radiation is output while such groups of radiation sources are switched, and charges are read out as described above, the total time for reading out the charges is as calculated by the following equation:

$$\text{Total Readout Time} = \left\{ \frac{\text{(Entire Area Readout Time)}}{(n+1)} \times \alpha \right\} + \text{(Entire Area Reset Time)}.$$

Therefore, high-speed readout is possible. In the equation, the term "Entire Area Readout Time" means a time period required to read out charge signals by sequentially switching all of the scan lines. The sign "$\alpha$" represents an overlap ratio of irradiation ranges of adjacent groups of radiation sources. The term "Entire Area Reset Time" means a time period required to reset all of charge storage portions.

When each of the radiation sources are controlled, based on the image correction data, in such a manner that the intensity of radiation output from each of the radiation sources belonging to the same group of radiation sources is similar to each other, it is possible to prevent the intensity of radiation output from each radiation source belonging to the same group of radiation sources from becoming uneven.

When the radiation sources are arranged in such a manner that each total pixel value obtained by adding pixel signals at the same pixel positions of a plurality of pieces of image correction data obtained by the image data obtainment unit is substantially similar to each other, and the divergence angle of the fan beam output from each of the radiation sources is set, and the intensity of the fan beam output from each of the radiation sources is controlled, it is possible to obtain radiographic image data that is more uniform (even).

DESCRIPTION OF THE PREFERRED EMBODIMENTS

Figure 1:
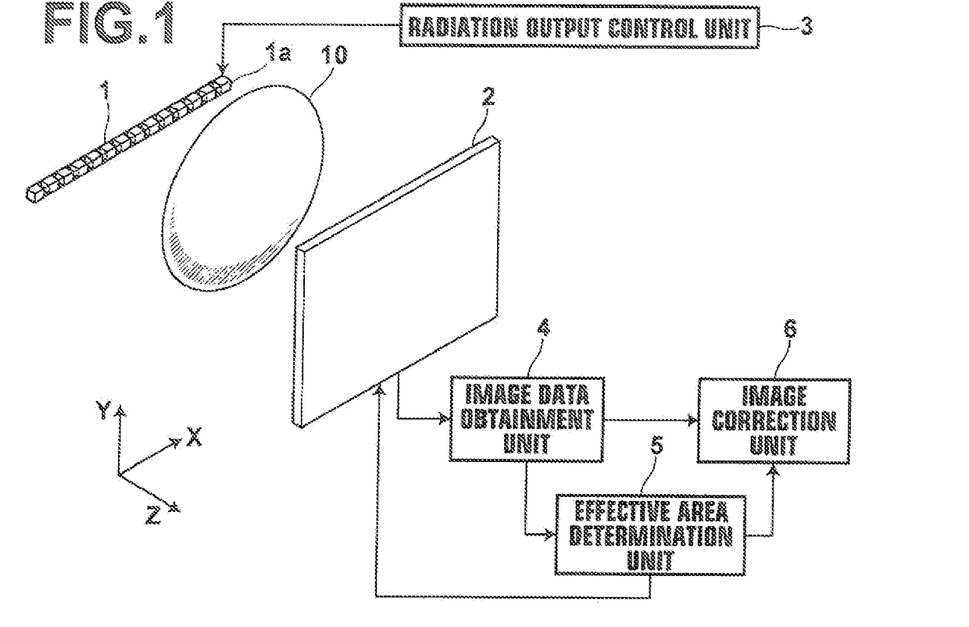
FIG. 1 a schematic diagram illustrating the configuration of a radiographic apparatus according to an embodiment of the present invention.

Hereinafter, a radiographic apparatus according to an embodiment of the present invention will be described with reference to drawings. FIG. 1 is a schematic diagram illustrating the configuration of the radiographic apparatus of the present invention.

As illustrated in FIG. 1, the radiographic apparatus of the present invention includes a radiation output unit 1, a radiographic image detector 2, a radiation output control unit 3, an image data obtainment unit 4, an effective area determination unit 5, and an image correction unit 6.

As illustrated in FIG. 1, the radiation output unit 1 includes a multiplicity of linearly-arranged radiation sources 1a, and each of the multiplicity of radiation sources 1a outputs a fan beam of radiation that has a wide divergence direction and a narrow divergence direction. The fan beams of radiation are output in such a manner that cross sections of the fan beams of radiation showing the wide divergence directions are parallel to each other. The radiation output from each of the radiation sources 1a passes through a subject 10, and is detected by the radiographic image detector 2. The multiplicity of radiation sources 1a are dispersedly arranged so that the radiation that has been output from each of the multiplicity of radiation sources 1a and has passed through the subject 10 forms a part of a projection image of the subject 10. In other words, a partial projection image of the subject 10 formed by the radiation output from each of the radiation sources 1a is combined, and a whole projection image of the subject 10 is generated.

Figure 2:
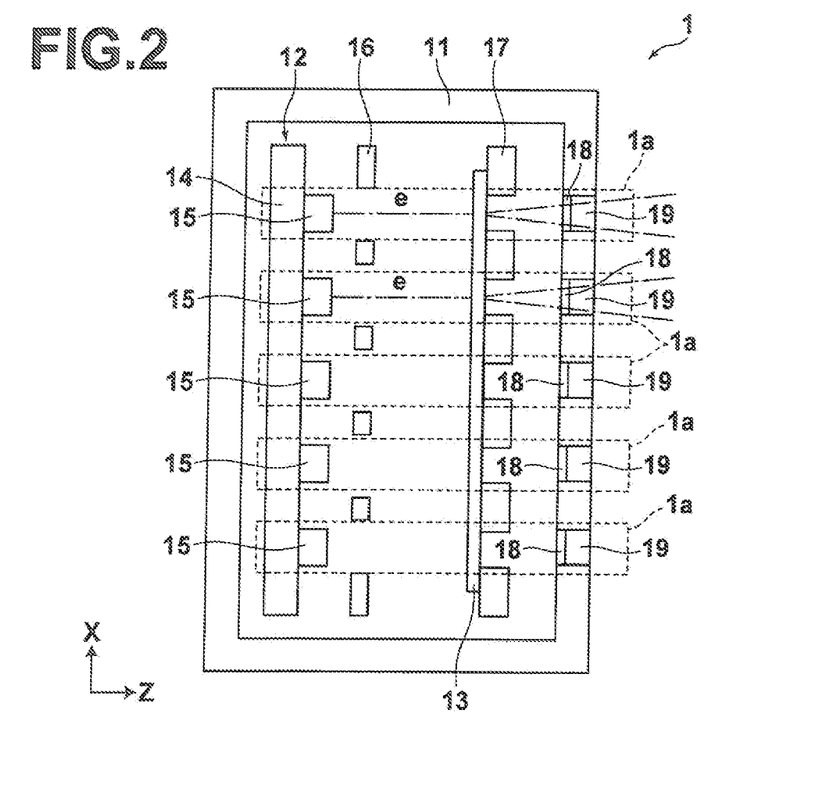
FIG. 2 is an X-Z cross section of a radiation output unit in the radiographic apparatus illustrated in FIG. 1.

FIG. 2 is a diagram illustrating the structure of the radiation output unit 1 in detail. FIG. 2 is an X-Z cross section of the radiation output unit 1 illustrated in FIG. 1.

As illustrated in FIG. 2, the radiation output unit 1 includes a housing 11 for forming a vacuum chamber. In the housing 11, a multi electron source 12 that outputs a multiplicity of electron beams and a target 13 are arranged. When the electron beams output from the multi electron source 12 hit the target 13, radiation is output from the target 13. Each of the radiation sources 1a includes an electron output device 15, and a combination of an electron lens 16, a part of the target 13, and a radiation extraction window 19 that correspond to the electron output device 15. The target 13 may be discretely arranged in such a manner that the target 13 corresponds to each of the electron output devices 15.

The multi electron source 12 includes a substrate 14 and a multiplicity of electron output devices 15. The multiplicity of electron output devices 15 are provided on the substrate 14 and output electron beams. Each of the electron output devices 15 is driven by the radiation output control unit 3.

Further, electron lenses 16 and radiation shield plates 17 are provided in the housing 11. The electron lens 16 condenses the electron beam output from each of the electron output devices 15 of the multi electron source 12. The radiation shield plate 17 forms the radiation output from the target 13 into a fan beam. Further, radiation extraction windows 19 are provided on a wall of the housing 11 in a radiation output direction. The radiation extraction window 19 includes a radiation transmission thin-film 18 that passes radiation. FIG. 2 schematically illustrates the structure of the radiation output unit 1. In FIG. 2, the number of the electron output devices 15 and the numbers of other elements, such as the electron lenses 16 and the radiation extraction windows 19, corresponding to the electron output devices 15 are smaller than the numbers of actual elements.

Figure 3:
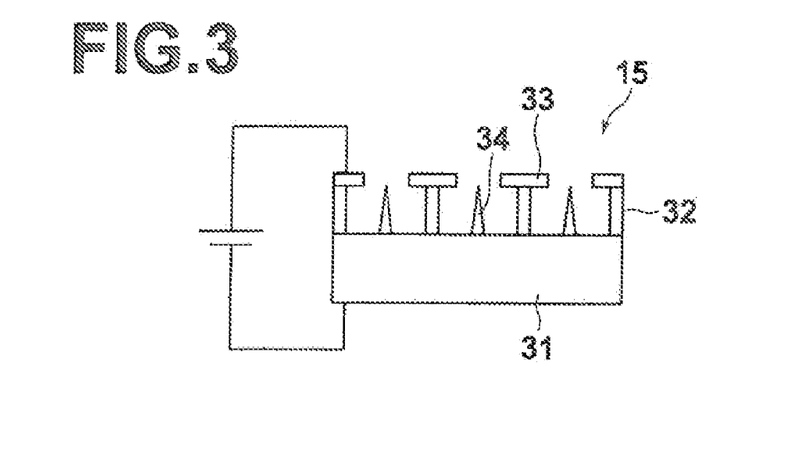
FIG. 3 is a diagram illustrating the structure of an electron output device in detail.

FIG. 3 is a diagram illustrating the structure of the electron output device 15 in detail. The electron output device 15 in the present embodiment is a cold-cathode-type electron output device. Specifically, insulators 32 and extraction electrodes 33 are provided on a device substrate 31 made of Si. Further, an emitter 34 is formed in a groove (channel, deposition or the like) of μm size substantially at a center between the extraction electrodes 33 adjacent to each other. The emitter 34 is made of carbon nanotubes, metal or semiconductor material, and the diameter of the tip (end) of the emitter 34 is dozens of nm. Electrons are output from the emitter 34 when the radiation output control unit 3 applies high voltage between the target 13 (anode) and the multi electron source 12 (cathode) and applies voltage to the extraction electrode 33 as illustrated in FIG. 3. The radiation output control unit 3 controls the voltage applied to the extraction electrode 33 to control output of electron beams from each of the electron output devices 15. In other words, the radiation output control unit 3 controls radiation output from each of the radiation sources 1a in such a manner.

The target 13 is structured as an anode, and is made of metal, such as Cu, W and Mo.

Figure 4A:
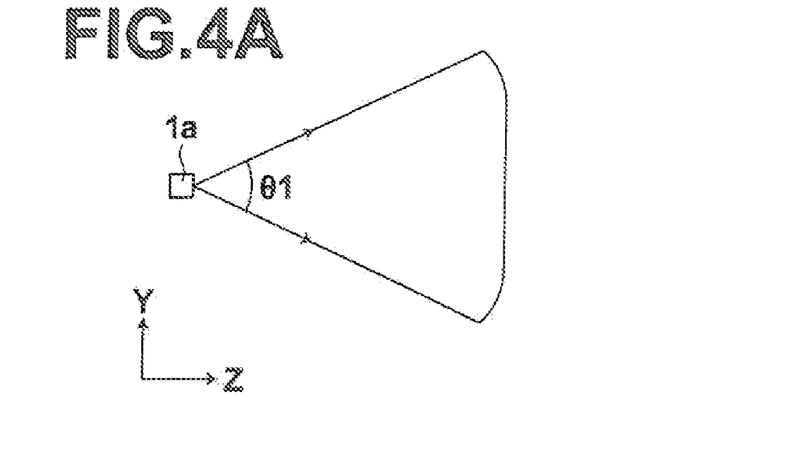
FIG. 4A is a cross section of a fan beam output from a radiation source showing a wide divergence direction of the fan beam.
Figure 4B:
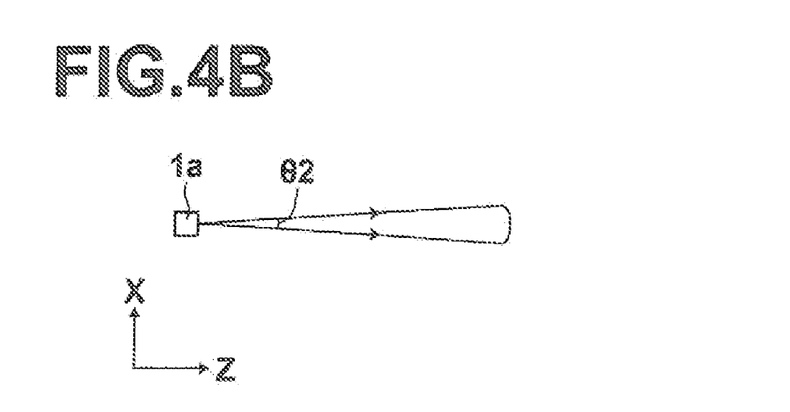
FIG. 4B is a cross section of a fan beam output from a radiation source showing a narrow divergence direction of the fan beam.

Each of the radiation sources 1a includes the electron output device 15 and the target 13 as described above, and outputs a fan beam of radiation that diverges widely in Y direction. FIG. 4A is an Y-Z cross section (a cross section in Y-Z direction) of radiation output from the radiation source 1a. FIG. 4B is an X-Z cross section (a cross section in X-Z direction) of radiation output from the radiation source 1a. As illustrated in FIG. 4A, radiation output from each of the radiation source 1a is a fan beam that has divergence angle $\theta1$ in Y direction. As illustrated in FIG. 4B, the fan beam has divergence angle $\theta2$ in X direction, and the divergence angles satisfy $\theta1>\theta2$.

The radiation output control unit 3 controls the radiation output unit 1 so that radiation is simultaneously output only from a part of the multiplicity of radiation sources 1a. The part of the multiplicity of radiation sources 1a output radiation the irradiation ranges of which neither overlap with each other nor are adjacent to each other on a radiographic image detector body 20. Further, the radiation output control unit 3 controls output of radiation by sequentially switching the groups of radiation sources 1a that output radiation. The control method will be described later.

Figure 5:
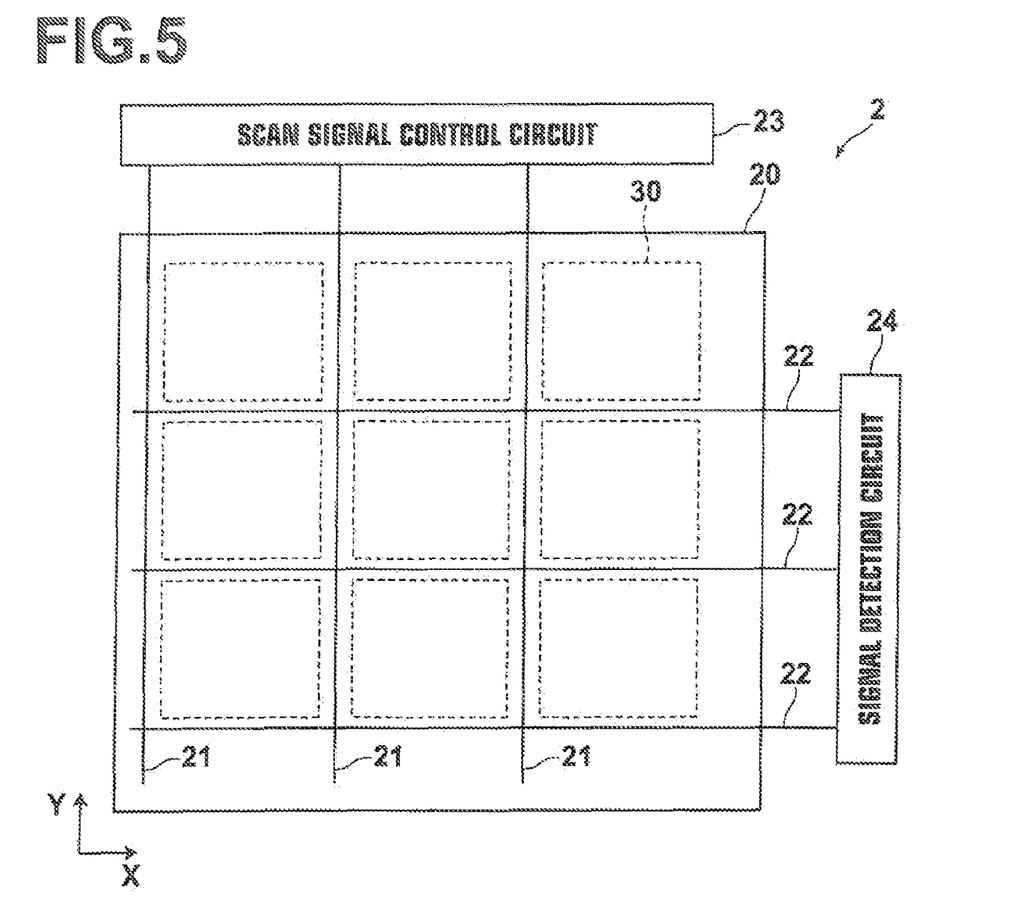
FIG. 5 is a schematic diagram illustrating the configuration of a radiographic image detector in the radiographic apparatus illustrated in FIG. 1.

As illustrated in FIG. 5, the radiographic image detector 2 includes the radiographic image detector body 20, a scan signal control circuit 23, and a signal detection circuit 24.

As illustrated in FIG. 5, in the radiographic image detector body 20, a plurality of scan lines 21 that extend in Y direction are provided. Further, a plurality of signal lines 22 that extend in X direction, and which intersect the scan lines 21, are provided. Further, a plurality of detection units 30 are two-dimensionally provided in such a manner to correspond to the intersections of the scan lines 21 and the signal lines 22.

Figure 6:
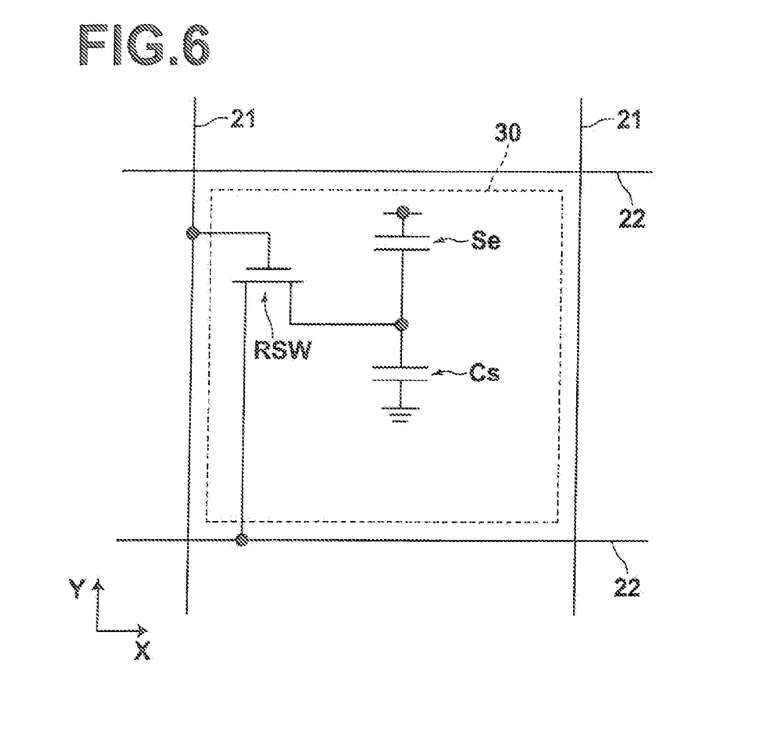
FIG. 6 is a diagram illustrating a schematic diagram illustrating the structure of a detection unit of the radiographic image detector illustrated in FIG. 5.

FIG. 6 is a diagram illustrating an example of the structure of the detection unit 30 provided in the radiographic image detector body 20 in detail.

As illustrated in FIG. 6, the detection unit 30 senses radiation output from the radiation output unit 1. The detection unit 30 includes a sensor unit Se, a charge storage portion Cs and a TFT (thin film transistor) type switch RSW. The sensor unit Se generates charges corresponding to the dose of radiation that has irradiated the sensor unit Se. The charge storage portion Cs stores the charges generated in the sensor unit Se. The TFT-type switch RSW is used to read out the charges stored in the charge storage portion Cs.

In the sensor portion Se, a photoelectric conversion layer that absorbs radiation and converts the radiation into charges is deposited. For example, the photoelectric conversion layer is made of a-Se (amorphous selenium) that contains selenium (Se) as the main component (for example, the Se content is greater than or equal to 50%). When the photoelectric conversion layer is irradiated with radiation, charges (electron-hole pairs) having a charge amount corresponding to the dose of radiation that has irradiated the photoelectric conversion layer are generated in the photoelectric conversion layer. Accordingly, the radiation that has irradiated the photoelectric conversion layer is converted into charges. It is not necessary that the sensor unit Se is made of a material, such as amorphous selenium, that directly converts radiation into charges. Alternatively, a phosphor material (fluorescent material) and a photoelectric conversion device (photodiode) may be used to indirectly convert radiation into charges. As the phosphor material, cadmium sulfate (GOS) activated with Tb or Eu, and cesium iodide (CsI) activated with Tl or Na are well known. In this case, radiation is converted into light by the phosphor material, and the light is converted into charges by a photodiode of a photoelectric conversion device using amorphous silicon, or the like.

The source of the switch RSW is connected to the signal line 22, and the drain of the switch RSW is connected to the charge storage portion Cs. Further, the gate of the switch RSW is connected to the scan line 21.

When the switch RSW connected to the signal line 22 is turned on, an electric signal corresponding to the amount of charges stored in the charge storage portion Cs flows into the signal line 22.

As illustrated in FIG. 5, each of the signal lines 22 is connected to a signal detection circuit 24 that detects the electric signal that has flowed into the signal lines 22. Further, each of the scan lines 21 is connected to a scan signal control circuit 23 that outputs a control signal for turning on/off the switch RSW to each of the scan lines 21.

The signal detection circuit 24 includes amplification circuits for amplifying input electric signals. The amplification circuit is provided for each of the signal lines 22. The signal detection circuit 24 amplifies the electric signal of each detection unit 30 that is input from each of the signal lines 22 by using the amplification circuit, and detects the amplified signal. Accordingly, the signal detection circuit 24 detects a pixel signal for each pixel that composes a radiographic image.

Further, the radiographic image detector body 20 and the radiation output unit 1 are arranged in such a manner that the wide divergence directions of the fan beams output from the radiation sources 1a and the directions in which the scan lines 21 extend (Y-direction) are the same.

The image data obtainment unit 4 obtains the radiographic image data detected by the radiographic image detector 2. The image obtainment unit 4 obtains radiographic image correction data and radiographic image data. The radiographic image correction data is detected by the radiographic image detector 2 without setting a subject between the radiation output unit 1 and the radiographic image detector 2. The radiographic image data is detected by the radiographic image detector 2 in a state in which the subject 10 is set between the radiation output unit 1 and the radiographic image detector 2.

The effective area determination unit 5 compares each pixel signal of the radiographic image correction data obtained by the image data obtainment unit 4 with a predetermined threshold value, and determines an effective area that has a value higher than the predetermined threshold value. The predetermined threshold value should prevent an influence of scattered X-rays by the detector per se or by objects that are present around the detector. Therefore, the predetermined threshold value may be appropriately determined, for example, at 10% of the value at the center of the beam.

The image correction unit corrects the radiographic image data obtained by the image data obtainment unit 4 by using the radiographic image correction data. A plurality of pieces of radiographic image data (radiographic image data representing a plurality of images) and a plurality of pieces of radiographic image correction data (radiographic image correction data representing a plurality of images) are obtained by sequentially switching the groups of the radiation sources 1a. Pixel signals at the same pixel positions of the plurality of pieces of radiographic image data are added to generate a piece of whole radiographic image data (whole radiographic image data representing an image). Pixel signals at the same positions of the plurality of pieces of radiographic image correction data are added to generate a piece of whole radiographic image correction data (whole radiographic image correction data representing an image). Further, the whole radiographic image data is corrected by using the whole radiographic image correction data. Specifically, the correction processing is performed by multiplying each addition pixel signal of the whole radiographic image data by the reciprocal of an addition pixel signal of the whole radiographic image correction data at the same pixel position as the position of the addition pixel signal of the whole radiographic image data.

Next, the action of the radiographic apparatus of the present embodiment will be described.

First, radiation is output from the radiation output unit 1 without setting the subject 10 between the radiation output unit 1 and the radiographic image detector 2. Radiographic image correction data is obtained (imaged) by detecting the radiation by the radiographic image detector 2.

Figure 7:
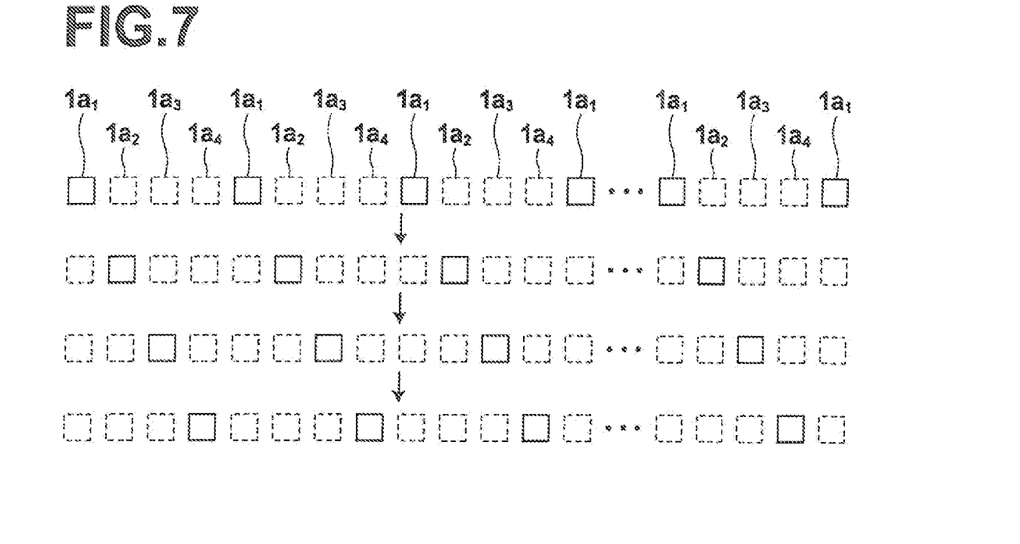
FIG. 7 is a diagram for explaining a control operation by sequentially switching groups of radiation sources.

The radiation output control unit 3 controls the radiation output unit 1 so that a fan beam of radiation is simultaneously output only from a part of the multiplicity of radiation sources 1a. The part of the radiation sources 1a output radiation the irradiation range of which neither overlap with each other nor are adjacent to each other on the radiographic image detector body 20. Further, radiation is sequentially output by sequentially switching the groups of radiation sources 1a. Specifically, for example as illustrated in FIG. 7, first, radiation is simultaneously output from a group of radiation sources $1a_1$, which are arranged at intervals of three radiation sources (in other words, arranged at every fourth position), and the radiographic image detector body 20 is irradiated with the radiation.

The radiation that has irradiated the radiographic image detector body 20 is converted into charges by the sensor unit Se of each detection unit 30 of the radiographic image detector body 20. The charges are stored in the charge storage portion Cs. Accordingly, a radiographic image is recorded.

Further, control signals for turning on the switches RSW of the detection units 30 are sequentially output from the scan signal control circuit 23 to each of the scan lines 21. The charges are read out from the detection units 30 connected to each of the scan lines 21 based on the control signals, and input to the signal detection circuit 24 through the signal lines 22. The signal detection circuit 24 detects the charges as pixel signals.

The pixel signals detected by the signal detection circuit 24 are obtained by the image data obtainment unit 4. The image data obtainment unit 4 generates apiece of radiographic image correction data, and outputs the piece of radiographic image correction data to the image correction unit 6 and the effective area determination unit 5.

Figure 8:
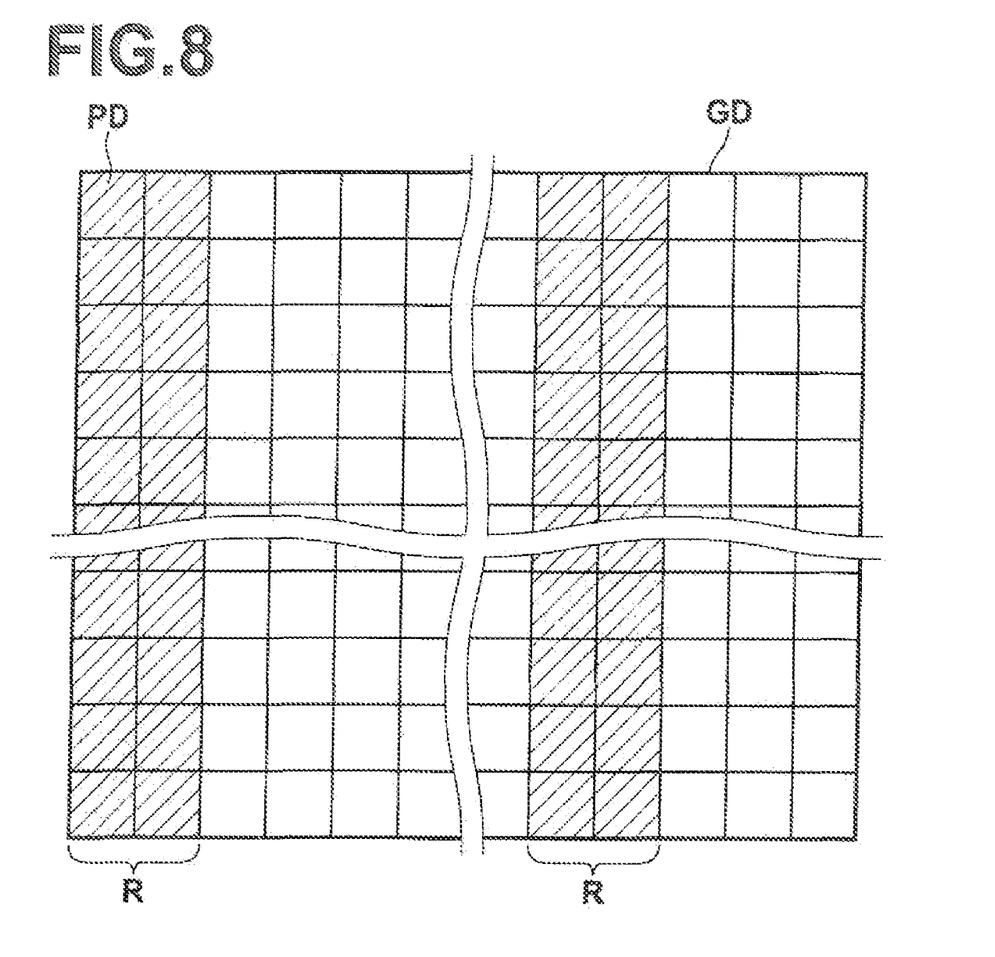
FIG. 8 is a schematic diagram illustrating radiographic image correction data GD, pixel signals PD, and effective areas R.

The image correction unit 6 stores the received radiographic image correction data. The effective area determination unit 5 compares each pixel signal of the received radiographic image correction data with a predetermined threshold value, and determines, as an effective area, an area of pixel signals that have values higher than the threshold value. FIG. 8 is a schematic diagram illustrating radiographic image correction data GD, pixel signals PD, and effective areas R. Information about the effective area determined by the effective area determination unit 5 is output to the scan signal control circuit 23 of the radiographic image detector 2.

Next, the radiation output control unit 3 controls the radiation output unit 1 so that radiation is output simultaneously from a group of radiation sources $1a_2$, which are adjacent to the radiation sources $1a_1$, as illustrated in FIG. 7. Further, the radiographic image detector body 20 is irradiated with the radiation.

Further, in a manner similar to the aforementioned operation, the image data obtainment unit 4 generates a piece of radiographic image correction data. The piece of radiographic image correction data is output to the image correction unit 6 and the effective area determination unit 5. The image correction unit 6 stores the radiographic image correction data. Further, information about the effective area determined by the effective area determination unit 5 is output to the scan signal control circuit 23 of the radiographic image detector 2.

Next, as illustrated in FIG. 7, radiation is output simultaneously from a group of radiation sources $1a_2$, which are adjacent to the radiation sources $1a_2$. Next, radiation is output simultaneously from a group of radiation sources $1a_4$, which are adjacent to the radiation sources $1a_3$. For each simultaneous output of radiation, an action and operation similar to the action and operation as described above is repeated. The image correction unit stores the radiographic image correction data. Further, information about the effective area determined by the effective area determination unit 5 is output to the scan signal control circuit 23 of the radiographic image detector 2.

As described above, a plurality of pieces of radiographic image correction data are obtained, and information about an effective area corresponding to each radiographic image correction data is obtained. Hereinafter, radiographic image correction data obtained by outputting radiation from a group of radiation sources $1a_n$ (n=1 to 4) will be referred to as $GD_n$ (n=1 to 4). Further, an effective area determined based on the radiographic image correction data $GD_n$ (n=1 to 4) will be referred to as Rn (n=1 to 4).

Next, radiation is output from the radiation output unit 1 in a state in which the subject 10 is set between the radiation output unit 1 and the radiographic image detector 2. Radiographic image data is obtained (imaged) by detecting the radiation by the radiographic image detector 2.

Specifically, processing is performed in a manner similar to the obtainment (imaging) of the radiographic image correction data, as described above. First, radiation is simultaneously output from the group of radiation sources $1a_1$, and the radiographic image detector body 20 is irradiated with radiation that has passed through the subject 10.

The radiation that has irradiated the radiographic image detector body 20 is converted into charges by the sensor unit Se in each of the detection units 30 of the radiographic image detector body 20. The charges are stored in the charge storage portion Cs, and a radiographic image of the subject 10 is recorded.

Figure 9:
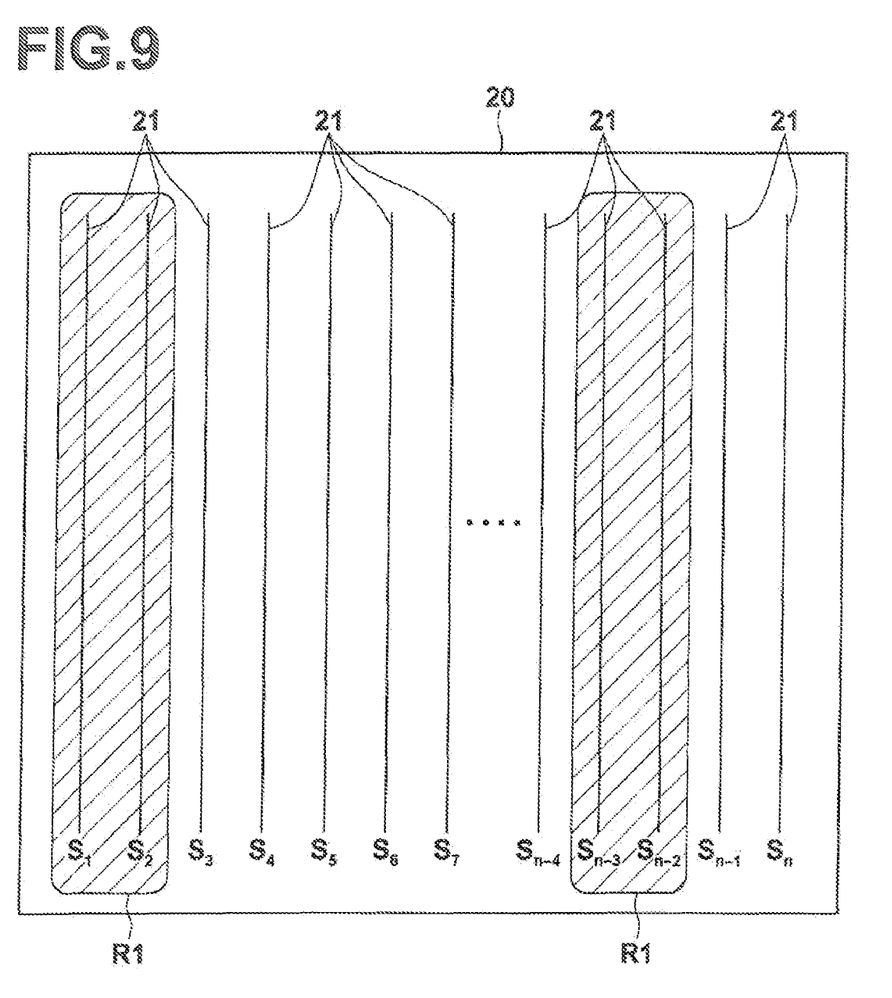
FIG. 9 is a diagram for explaining a method for reading out signals from a range of a radiographic image detector body 20 corresponding to effective area R1 and the remaining range of the radiographic image detector body 20.

The scan signal control circuit 23 outputs control signals for turning on the switches RSW of the detection units 30 to each of the scan lines 21. At this time, the scan signal control circuit 23 outputs the control signals based on information about the effective area that has been set in advance. Specifically, first, the scan signal control circuit 23 outputs control signals for turning on the switches RSW to each of the scan lines 21 connected to the column of detection units 30 on the radiographic image detection body 20 in a range that corresponds to the effective area R1 by sequentially switching the scan lines 21. For example, when shadow areas illustrated in FIG. 9 are a range on the radiographic image detector body 20 that corresponds to the effective area R1, control signals are output by sequentially switching the scan lines $S_1$, $S_2$, $S_{n-3}$, and $S_{n-2}$ in this order.

Further, charges are read out from the detection units 30 connected to each of the scan lines 21 based on the control signals, and the charges are input to the signal detection circuit 24 through the signal lines 22. The signal detection circuit 24 detects the charges as pixel signals.

The pixel signals detected by the signal detection circuit 24 are obtained by the image data obtainment unit 4, and the image data obtainment unit 4 generates apiece of radiographic image data. The generated piece of radiographic image data is output to the image correction unit 6. At this time, the radiographic image data is generated by regarding, as zero (0), pixel signals corresponding to detection units 30 outside the range of the radiographic image detector body 20 that corresponds to the effective area R1.

After the piece of radiographic image data is obtained as described above, the scan signal control circuit 23 outputs control signals for turning on the switches RSW. The control signals are output simultaneously to all of the scan lines 21 connected to the columns of detection units 30 outside the range of the radiographic image detector body 20 that corresponds to the effective area R1 to reset the charges stored in the detection units 30. For example, when shadow areas illustrated in FIG. 9 are a range on the radiographic image detector body 20 that corresponds to the effective area R1, control signals are simultaneously output to scan lines $S_3$ through $S_{n-4}$, scan line $S_{n-1}$, and $S_n$.

Next, radiation is simultaneously output from a group of radiation sources $1a_2$, which are adjacent to the radiation sources $1a_1$, and the radiographic image detector body 20 is irradiated with radiation that has passed through the subject 10.

The radiation that has irradiated the radiographic image detector body 20 is converted into charges by the sensor unit Se of each of the detection units 30 of the radiographic image detector body 20. The charges are stored in the charge storage portion Cs, and a radiographic image of the subject 10 is recorded.

The scan signal control circuit 23 outputs control signals for turning on the switches RSW to each of the scan lines 21 connected to the columns of detection units 30 within the range of the radiographic image detection body 20 that corresponds to effective area R2 by sequentially switching the scan lines 21.

Further, charges are read out from the detection units 30 connected each of the scan lines 21 based on the control signals. The charges are input to the signal detection circuit 24 through the signal lines 22. The signal detection circuit 24 detects the charges as pixel signals.

The pixel signals detected by the signal detection circuit 24 are obtained by the image data obtainment unit 4, and the image data obtainment unit 4 generates a piece of radiographic image data. The radiographic image data is output to the image correction unit 6. At this time, the radiographic image data is generated by regarding, as zero (0), pixel signals corresponding to detection units 30 outside the range of the radiographic image detector body 20 that corresponds to the effective area R2.

After the piece of radiographic image data is obtained as described above, the scan signal control circuit 23 outputs control signals for turning on the switches RSW. The control signals are output simultaneously to all of the scan lines 21 connected to the columns of detection units 30 outside the range of the radiographic image detector body 20 that corresponds to the effective area R2 to sequentially reset the charges stored in the detection units 30.

Next, radiation is simultaneously output from a group of radiation sources $1a_3$, which are adjacent to the radiation sources $1a_2$. Next, radiation is simultaneously output from a group of radiation sources $1a_4$, which are adjacent to the radiation sources $1a_3$. For output of radiation from each group, an action and operation similar to the action and operation as described above is repeated. Accordingly, the radiographic image data is stored in the image correction unit 6.

As described above, a plurality of pieces of radiographic image data are obtained. Hereinafter, radiographic image data obtained by outputting radiation from a group of radiation sources $1a_n$ (n=1 to 4) will be referred to as $HGD_n$ (n=1 to 4).

As described above, four pieces of radiographic image correction data $GD_n$ and four pieces of radiographic image data $HGD_n$ are stored in the image correction unit 6.

Next, the image correction unit 6 generates a piece of whole radiographic image data by adding pixel signals at the same pixel positions of the four pieces of radiographic image data $HGD_n$. Further, the image correction unit 6 generates a piece of whole radiographic image correction data by adding pixel signals at the same pixel positions of the four pieces of radiographic image correction data $GD_n$. Further, the image correction unit 6 corrects the piece of whole radiographic image data by using the piece of whole radiographic image correction data. Specifically, the correction processing is performed by multiplying each addition pixel signal of the whole radiographic image data by the reciprocal of an addition pixel signal of the whole radiographic image correction data at the same pixel position as the position of the addition pixel signal of the whole radiographic image data.

Further, the image correction unit 6 outputs the whole radiographic image data after correction, and a visible image based on the corrected whole radiographic image data is displayed on a monitor (not illustrated), or printed on a predetermined recording medium, or the like.

Further, in the radiographic apparatus according to the aforementioned embodiment, each of the radiation sources $1a$ may be controlled, based on the radiographic image correction data $GD_n$ obtained as described above, in such a manner that the intensity of radiation output from each of the radiation sources $1a$ belonging to the same group of radiation sources $1a$ is similar to each other.

Figure 10:
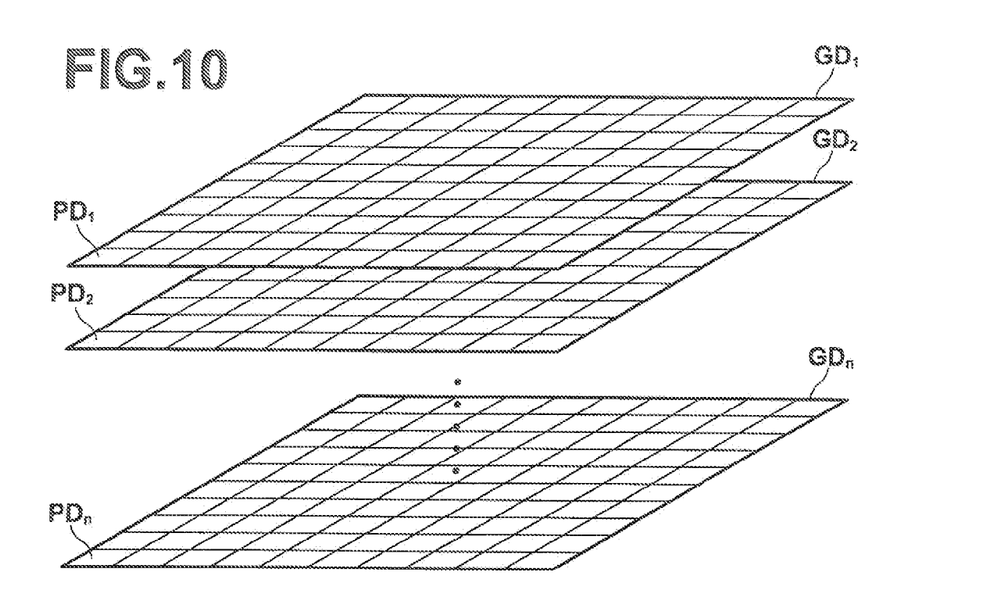
FIG. 10 is a schematic diagram illustrating a plurality of pieces of radiographic image correction data $GD_1$ through $GD_n$ and pixel signals $PD_1$ through $PD_n$ at the same pixel positions.

It is desirable that a piece of whole radiographic image correction data is generated by adding pixel signals at the same pixel positions of a plurality of pieces of radiographic image correction data $GD_n$. Further, it is desirable that an interval (distance) between adjacent radiation sources $1a$ in the radiation output unit 1, divergence angles θ1 and θ2 of a fan beam output from each of the radiation sources $1a$, or the like is set so that the value of each of the addition image signals of the whole radiographic image correction data is the same.

In the radiographic apparatus of the aforementioned embodiment, radiographic image data is obtained by reading out charge signals only from detection units 30 in a range corresponding to an effective area that has been set in advance. Further, detection units 30 on the outside of the range are reset. However, it is not necessary that processing is performed in such a manner. For example, after radiation is output from a predetermined group of radiation sources, all of pixel signals may be obtained by outputting control signals to all of the scan lines 21 by sequentially switching the scan lines 21 in a manner similar to obtainment of the radiographic image correction data. After all of the pixel signals are obtained, pixel signals only in a range corresponding to a predetermined effective area may be extracted from all of the pixel signals to generate a piece of radiographic image data.

Figure 11:
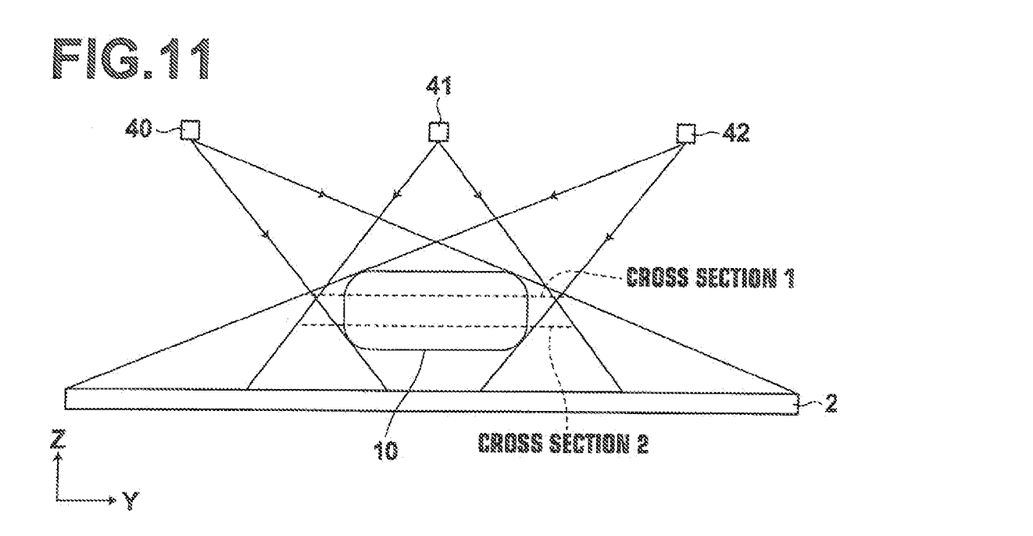
FIG. 11 is a diagram illustrating a structure in which a plurality of arrays of radiation sources are provided.

Further, in the radiographic apparatus of the aforementioned embodiment, the radiation output unit 1 is structured by linearly arranging the radiation sources $1a$. However, it is not necessary that the radiation output unit 1 is structured in such a manner. For example, the radiation sources $1a$ may be arranged in a plurality of arrays (rows, columns, or lines) that are arranged parallel to each other with respect to a direction (Y direction) perpendicular to the direction (X direction) in which the arrays of the radiation sources $1a$ extend. In FIG.

11, the arrays of the radiation sources 1a extend in the thickness direction of the paper (the direction perpendicular to the paper surface).

Further, as illustrated in FIG. 11, radiation may be output to the subject 10 from a radiation source array 40, a radiation source array 41, and a radiation source array 42 at different angles from each other. Further, whole radiographic image data after correction may be obtained for each of the radiation source arrays 40, 41 and 42 in a manner similar to the aforementioned method, and a tomographic image (cross-sectional image) of the subject 10 may be generated based on the plurality of pieces of whole radiographic image data after correction. The tomographic image may be generated, for example, by a so-called shift-and-add method. In the shift-and-add method, the tomographic image is generated by shifting the plurality of whole radiographic image data after correction to a desirable cross-sectional position of the subject and by adding the shifted data. The shift amount of each of the whole radiographic image data after correction is controlled, and tomographic images corresponding to cross section 1 and cross section 2, as illustrated in FIG. 11, can be generated.

Further, in the radiographic apparatus of the present embodiment, the radiographic image detector as illustrated in FIG. 5 is used. However, the structure of the radiographic image detector is not limited. Other kinds of radiographic image detectors, such as a direct-conversion type flat-panel detector, an indirect-conversion type flat-panel detector, and an imaging plate, that are used in conventional radiographic apparatuses may be used.

What is claimed is:

1. A radiographic apparatus comprising:
a radiation output unit including a multiplicity of dispersedly-arranged radiation sources each outputting a fan beam of radiation that has a wide divergence direction and a narrow divergence direction in such a manner that cross sections of the fan beams of radiation that show the wide divergence directions are parallel to each other;
a radiographic image detector that detects the fan beam of radiation output from each of the multiplicity of dispersedly-arranged radiation sources of the radiation output unit;
a radiation output control unit that controls the radiation output unit in such a manner that the fan beams of radiation are output simultaneously only from each group of radiation sources, which are a part of the multiplicity of dispersedly-arranged radiation sources having irradiation ranges of the fan beams of radiation that neither overlap with each other nor are adjacent to each other on the radiographic image detector, and in such a manner that the groups of radiation sources are sequentially switched to output the radiation;
an image data obtainment unit that obtains image correction data corresponding to each of the groups of radiation sources, the image correction data being sequentially detected by the radiographic image detector by sequentially outputting the fan beams of radiation to the radiographic image detector while the radiation output control unit sequentially switches the groups of radiation sources without setting a subject between the radiation output unit and the radiographic image detector;
an effective area determination unit that determines, for each image correction data obtained by the image data obtainment unit, an effective area that has a value higher than a predetermined threshold value; and
an image correction unit that corrects, based on the image correction data corresponding to each of the groups of radiation sources, radiographic image data corresponding to each of the groups of radiation sources that has been sequentially detected by the radiographic image detector by sequentially outputting the fan beams of radiation to the radiographic image detector while the radiation output control unit sequentially switches the groups of radiation sources in a state in which a subject is set between the radiation output unit and the radiographic image detector and that has been obtained based on the effective area.

2. A radiographic apparatus, as defined in claim 1, the radiographic image detector includes charge generation portions that generate charges corresponding to irradiation with the radiation, a multiplicity of two-dimensionally-arranged charge storage portions that store the charges generated in the charge generation portions, a multiplicity of signal lines each provided for each row of the multiplicity of two-dimensionally-arranged charge storage portions, and through which charge signals representing the charges stored in the multiplicity of two-dimensionally-arranged charge storage portions flow out, a multiplicity of switch devices that switch connections/disconnections between the multiplicity of signal lines and the multiplicity of two-dimensionally-arranged charge storage portions that correspond to the multiplicity of signal lines, the multiplicity of switch devices being provided for the charge storage portions respectively, and a multiplicity of scan lines each provided for each column of the multiplicity of two-dimensionally-arranged charge storage portions in such a manner that the multiplicity of scan lines are perpendicular to the multiplicity of signal lines, and through which control signals for turning on/off the multiplicity of switch devices are output, wherein the radiographic image detector and the radiation output unit are arranged in such a manner that the wide divergence directions of the fan beams of radiation and the directions in which the multiplicity of scan lines extend are the same.

3. A radiographic apparatus, as defined in claim 1, further comprising a scan signal control unit, wherein the scan signal control unit reads out charge signals from charge storage portions on the radiographic image detector within a range corresponding to the effective area by sequentially outputting control signals for turning on switch devices to each of scan lines connected to columns of the charge storage portions within the range corresponding to the effective area, and after reading out the charge signals, resets charge storage portions on the radiographic image detector outside the range corresponding to the effective area by simultaneously outputting control signals for sequentially turning on switch devices to a plurality of scan lines that are connected to columns of the charge storage portions outside the range corresponding to the effective area.

4. A radiographic apparatus, as defined in claim 1, further comprising a radiation source control unit that controls, based on the image correction data, each of the multiplicity of radiation sources in such a manner that the intensity of radiation output from each of the radiation sources belonging to the same group of radiation sources is similar to each other.

5. A radiographic apparatus, as defined in claim 1, wherein the radiation sources are arranged in such a manner that each total pixel value obtained by adding pixel signals at the same pixel positions of a plurality of pieces of image correction data obtained by the image data obtainment unit is substantially similar to each other, and wherein the divergence angle of the fan beam output from each of the radiation sources is set, and the intensity of the fan beam is controlled.

* * * * *